US00PP24276P3

(12) United States Plant Patent
Olesen

(10) Patent No.: US PP24,276 P3
(45) Date of Patent: Mar. 4, 2014

(54) GROUND COVER ROSE PLANT NAMED 'POULCOT011'

(50) Latin Name: ***Rosa* hybrid**
Varietal Denomination: Poulcot011

(75) Inventor: Mogens Nyegaard Olesen, Fredensborg (DK)

(73) Assignee: Poulsen Roser A/S

( * ) Notice: Subject to any disclaimer, the term of this patent is extended or adjusted under 35 U.S.C. 154(b) by 0 days.

(21) Appl. No.: 13/507,041

(22) Filed: May 31, 2012

(65) Prior Publication Data

US 2013/0326737 P1 Dec. 5, 2013

(51) Int. Cl.
*A01H 5/00* (2006.01)

(52) U.S. Cl.
USPC ..... Plt./102

(58) Field of Classification Search
USPC ..... Plt./101, 102, 105, 106, 107
See application file for complete search history.

*Primary Examiner* — Kent L Bell

(57) ABSTRACT

A new garden rose plant of the ground cover class which has abundant, orange pink flowers and attractive foliage. This new and distinct variety has shown to be uniform and stable in the resulting generations from asexual propagation.

1 Drawing Sheet

Botanical designation: *Rosa* hybrid.
Variety denomination: 'Poulcot011'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2002 and the resulting seeds were planted in a controlled environment in Fredensborg, Denmark. The new variety, named 'Poulcot011', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant orange pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcot011' from all other varieties of which we are aware.

As part of the rose development program, Mogens N. Olesen germinated the seeds from the aforementioned hybridization during winter of 2002 and conducted evaluations on the resulting seedlings in a controlled environment in Fredensborg, Denmark. 'Poulcot011' was selected in the spring of 2003 by the inventor as a single plant from the progeny of the aforementioned hybridization.

Asexual reproduction of 'Poulcot011' by traditional budding and rooted cuttings was first done by Mogens N. Olesen in the nursery in Fredensborg, Denmark in July, 2003. This initial and other subsequent asexual propagations conducted in controlled environments have demonstrated that the characteristics of 'Poulcot011' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcot011'.

Specifically illustrated in the drawing are flowers at various stages of development, flower in parts, leaves, and stems.

DETAILED DESCRIPTION OF THE VARIETY

The following is a description of 'Poulcot011', as observed in its growth in a field nursery in Bakersfield, Calif. 2 years of age, and were grown on their own roots. Color references are made using The Royal Horticultural Society (London, England) Colour Chart, 2001, except where common terms of color are used.

For a comparison, several physical characteristics of the rose variety 'Poulcot010', U.S. Plant Pat. No. 22,713 are compared to 'Poulcot011' in Chart 1.

CHART 1

| | 'Poulcot011' | 'Poulcot010' |
|---|---|---|
| Petal Count | 15 | 15 |
| Flower Diameter | 35 to 40 mm | 40 to 50 mm |
| General Tonality of Flower Color | Red Group 38B with Yellow Group 8B | Yellow Group 13C with intonations of Orange-Red Group 35A |

Flower and Flower Bud

Blooming habit: Continuous.
Flower bud:

*Size.*—Upon opening, 16 mm in length from base of receptacle to end of bud. Bud diameter is 8 mm.

*Bud form.*—Ovoid.

*Bud color.*—As sepals divide petals are Orange-Red Group 30A to Orange Group 29A.

*Sepal inner surface.*—Color: Yellow-Green Group 144C. Surface: Smooth.

*Sepal outer surface.*—Color: Yellow-Green Group 144A. Intonations of Greyed-Red Group 178A observed. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—20 mm long by 7 mm wide.

*Receptacle.*—Texture: Smooth. Size: 5 mm in height by 4 mm wide. Color: Yellow-Green Group 144A. Anthocyanic pigments the color of Greyed-Red Group 178A observed. Shape: Campanulate.

*Pedicel.*—Surface: Smooth. Length: 18 mm. Diameter: 2 mm on average. Color: Yellow-Green Group 144A. Strength: Moderate.

*Peduncle.*—Length: 4 to 16 cm. Diameter: 3 to 4 mm. Color: Yellow-Green Group 144A.

Flower bud development: Flower buds are borne in clusters of 50 to 60 flower buds per stem, resembling a panicle.

Flower bloom:

*Fragrance.*—Light spicy scent.

*Duration.*—The blooms have a duration on the plant of approximately 7 to 10 days. Petals fall cleanly away from plant after flowers have fully matured.

*Size.*—Flower diameter is 35 to 40 mm when open. Flower depth is 15 mm.

*Flower shape.*—Single, fully open, and almost flat.

*Shape of flower, side view.*—The upper and lower portion are flattened convex in shape.

Petalage: Under normal conditions, flowers have 15 petals total, 1 to 3 of which are petaloids.

General tonality of flower: Open flowers are Red Group 38B with Yellow Group 8B.

Petal color:

*Upon opening.*—Upper and lower surface is Red Group 38B blending with Yellow Group 8B at the basal zone.

*After opening.*—Upper and lower surface is Red Group 38B blending with Yellow Group 8B at the basal zone.

Petals:

*Reflex.*—Weak.

*Margin.*—Entire and uniform. Weak undulations of margin observed.

*Shape.*—Generally narrow and elliptic. Apex shape: Rounded. Base shape: Acute.

*Size.*—19 mm (l)×19 mm (w) on average.

*Texture.*—Smooth.

*Thickness.*—Thin.

Petaloids:

*Size.*—6 mm (l) by 5 mm (w).

*Quantity.*—1 to 3.

*Shape.*—Symmetric. Apex is rounded. Base is acute.

*Color.*—Upper and lower surface is Red Group 38B blending with Yellow Group 8B at the basal zone.

Reproductive organs:

*Pollen.*—None observed.

*Anthers.*—Size: Approximately 1 mm in length. Color: Greyed-Orange Group N170A. Quantity: 35 on average.

*Filaments.*—Color: Yellow Group 8A. Length: 3 mm.

*Pistils.*—Length: 3 mm. Quantity: 15 on average.

*Stigmas.*—Color: Greyed-Yellow Group 162A.

*Styles.*—Color: Red-Purple Group 58B.

*Location of stigmas.*—Level in location relative to the length of the filaments and the height of the anthers.

*Hips.*—None Observed.

Plant

Plant growth: Low growing, bushy. Plants are 40 cm in height, and 40 cm wide.

Stems:

*Color.*—Juvenile growth: Yellow-Green Group 144A. Mature growth: Yellow-Green Group 144A.

*Length.*—On average, canes are 25 cm from the base of the plant to the flowering portion.

*Diameter.*—9 mm.

*Internodes.*—On mature canes, there is an average distance of 25 mm between nodes.

*Surface texture.*—Young wood: Smooth. Older wood: Smooth.

Long prickles:

*Incidence.*—10 prickles per 10 cm of stem.

*Size.*—Average length of prickles on mature stems is 13 mm.

*Shape.*—Upper portion is linear. Lower portion is deep concave.

*Color.*—Juvenile prickles: Yellow-Green Group 144D with Greyed-Red Group 178B. Mature prickles: Greyed-Red Group 178A.

Plant foliage:

*Compound leaf.*—80 mm (l)×50 (w).

*Quantity.*—3 leaves per 10 cm of stem on average.

*Leaf bearing angle to the stem.*—60 degrees.

*Color of juvenile foliage.*—Upper side: Yellow-Green Group 147A. Lower side: Yellow-Green Group 147B. Anthocyanin: At margins, Greyed-Red Group 178A.

*Color of mature foliage.*—Upper side: Yellow-Green Group 147A. Lower side: Yellow-Green Group 147B.

Plant leaves and leaflets:

*Stipules.*—Size: 11 mm in length. Quantity: 2 per compound leaf. Shape: Linear, slightly broad based with outward extending apices. Margins: Finely serrated. Color: Yellow-Green Group 144A.

*Petiole.*—Length: 11 mm. Diameter: 2 mm.

*Upper surface.*—Yellow-Green Group 144A.

*Lower surface.*—Yellow-Green Group 144B.

*Rachis.*—Length: 42 mm on average. Upper surface: Yellow-Green Group 144A. Lower surface: Yellow-Green Group 144B.

*Leaflet.*—Quantity: Normal number of leaflets per leaf in middle of the stem is 7 leaflets. Margins: Serrated. Size: Average size of the terminal leaflet on normal leaves is 27 mm in length by 15 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Ground Cover rose class named 'Poulcot011', substantially as illustrated and described herein, due to its abundant orange pink flowers, disease resistance, and extended period of bloom.

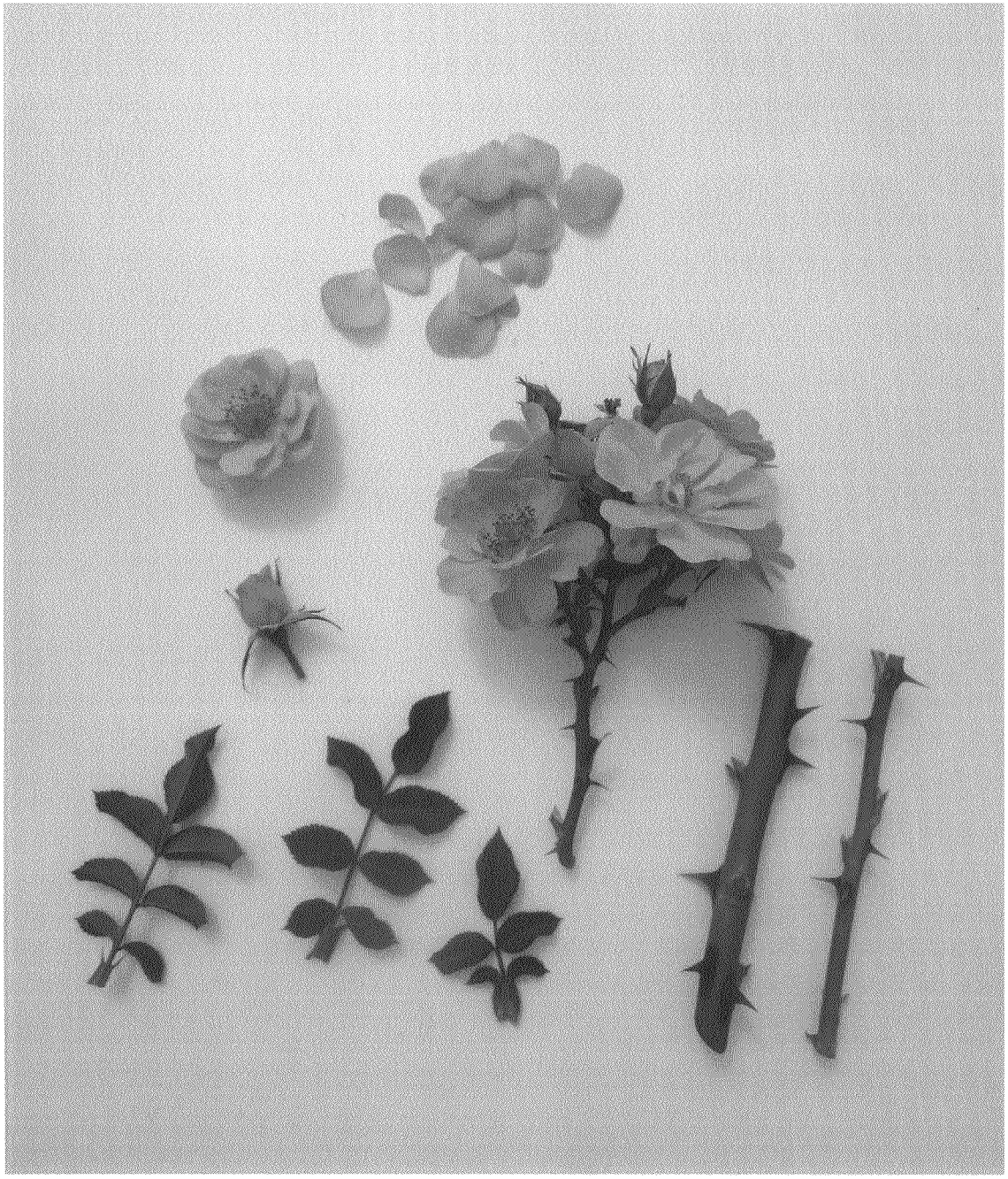

* * * * *